(12) United States Patent
Yang et al.

(10) Patent No.: US 6,441,348 B1
(45) Date of Patent: Aug. 27, 2002

(54) HEAT TREATMENT APPARATUS AND METHOD OF USING SAME

(75) Inventors: Zheng Qing Yang, Kowloon (HK); Yuan Kun Zhang, Nansing (CN)

(73) Assignee: Raymond Industrial Limited, Shatin (HK)

(*) Notice: Subject to any disclaimer, the term of this patent is extended or adjusted under 35 U.S.C. 154(b) by 0 days.

(21) Appl. No.: 09/759,021

(22) Filed: Jan. 10, 2001

(51) Int. Cl.[7] .............................. A61F 7/00; A61K 7/50
(52) U.S. Cl. ................................... 219/439; 607/86
(58) Field of Search ............................ 219/439, 430, 219/436, 437, 441, 530, 540; 607/86, 114; 392/444, 447

(56) References Cited

U.S. PATENT DOCUMENTS

| | | | | |
|---|---|---|---|---|
| 2,463,329 A | * | 3/1949 | Stansbury | 219/422 |
| 2,904,037 A | * | 9/1959 | Cassidy | 607/86 |
| 4,149,536 A | | 4/1979 | Villard | 128/261 |
| 4,632,115 A | | 12/1986 | Bernardini | 128/370 |
| 4,696,303 A | | 9/1987 | Bernardini | 128/402 |
| 4,880,415 A | | 11/1989 | Urakami | 604/291 |
| 5,674,268 A | | 10/1997 | Riazi | 607/96 |
| 5,891,116 A | | 4/1999 | Mast | 604/290 |
| 6,184,500 B1 | * | 2/2001 | Glucksman | 219/432 |

FOREIGN PATENT DOCUMENTS

JP 11-56893 * 3/1999

* cited by examiner

Primary Examiner—Joseph Pelham
(74) Attorney, Agent, or Firm—Marshall, Gerstein & Borun

(57) ABSTRACT

Apparatus for melting a solid mass of wax is disclosed. The apparatus comprises a housing having a base and a sidewall. A heating element is disposed inside the housing and positioned near the base for generating heat. A heat conducting plate is positioned above the heating element for conducting the heat from the heating element to melt a bottom surface of the solid mass of wax. A control circuit is provided for automatically controlling a temperature of the heating element. In operation, the apparatus performs a fast and efficient method for melting wax. A bottom surface of the solid wax mass is melted into a bottom layer of melted wax using the heating element. The heating element is shut off once the bottom layer of melted wax reaches a desired volume. A portion of the bottom layer of melted wax is transferred to a top surface of the solid wax mass to create a top layer of melted wax, so that a remaining core of solid wax mass is disposed between the top and bottom layers of melted wax. The remaining core of solid wax mass is then melted using latent heat in the top and bottom layers of melted wax, thereby to create a volume of melted wax at a usable temperature.

17 Claims, 2 Drawing Sheets

US 6,441,348 B1

HEAT TREATMENT APPARATUS AND METHOD OF USING SAME

FIELD OF THE INVENTION

The present invention generally relates to heat therapy products and, more particularly, to heat treatment apparatus using a meltable medium.

BACKGROUND OF THE INVENTION

Heat treatment apparatus for providing therapeutic relief to a desired body part are generally known in the art. Such apparatus are typically provided in the form of a bath comprising a housing and a removable container sized to receive the hands or feet of user. A meltable medium, such as paraffin wax, is deposited into the container, and provides a therapeutic affect when heated.

The paraffin wax is typically in a solid state when at normal room temperature. To melt the wax, a heater is provided in the housing below the container and is sized to generate heat sufficient to melt the paraffin wax inside the container. When the paraffin wax has been completely melted and has obtained a desired temperature of approximately 127° to 135° F. (53°–57° C.), the user places the hands, feet, or other desired body part in the melted wax bath. The heated paraffin wax bath is known to provide moist heat treatment that softens and soothes dry and cracked skin, and eases stiff joints. The paraffin wax used in the bath may be pure, or may include additives which provide aromatherapy, such as a citrus blend fragrance.

While conventional heat treatment baths are capable of providing the intended therapeutic effect, they typically require excessively long periods of time in which to melt the paraffin wax. The known conventional apparatus use a heating element to first heat the container. The heated container, in turn, heats the solid paraffin wax contained therein, thereby melting the wax. The wax will melt from the bottom up until the entire mass of solid wax is melted. Consequently, the conventional heat treatment baths may require several hours to completely melt the paraffin wax. Such waiting periods are entirely impractical for many people.

Thus, there is a need for heat treatment apparatus which quickly and efficiently melts paraffin wax to a desired working temperature.

SUMMARY OF THE INVENTION

In accordance with certain aspects of the present invention, a method of melting a mass of solid wax in a bath is provided, in which the bath comprises a housing with a base and a sidewall, and a heating element disposed inside the housing near the base. The method comprises melting a bottom surface of the solid wax mass into a bottom layer of melted wax using the heating element and shutting off the heating element once the bottom layer of melted wax reaches a desired volume. A portion of the bottom layer of melted wax is then transferred to a top surface of the solid wax mass to create a top layer of melted wax, a remaining core of solid wax mass being disposed between the top and bottom layers of melted wax. The remaining core of solid wax mass is melted using latent heat in the top and bottom layers of melted wax, thereby to create a volume of melted wax at a usable temperature.

In accordance with additional aspects of the present invention, apparatus for melting a solid mass of wax is provided comprising a housing having a base and a sidewall, and a heating element disposed inside the housing and positioned near the base for generating heat. A heat conducting plate is positioned above the heating element for conducting the heat from the heating element to melt a bottom surface of the solid mass of wax. A control circuit is provided for automatically controlling a temperature of the heating element.

In accordance with further aspects of the present invention, apparatus is provided for melting a solid mass of wax. The apparatus comprises a housing having a base and a sidewall, a heating element disposed inside the housing and positioned near the base for generating heat, and a heat conducting plate positioned above the heating element for conducting the heat from the heating element to melt a bottom surface of the solid mass of wax. An enclosure is attached to the housing base, and a control circuit for automatically controlling a temperature of the heating element is disposed inside the enclosure. An insulating layer is positioned between the heating element and the enclosure for protecting the enclosure from excessive heat.

Other features and advantages are inherent in the apparatus claimed and disclosed or will become apparent to those skilled in the art from the following detailed description and its accompanying drawings.

DETAILED DESCRIPTION OF THE PREFERRED EMBODIMENTS

Figure 1:
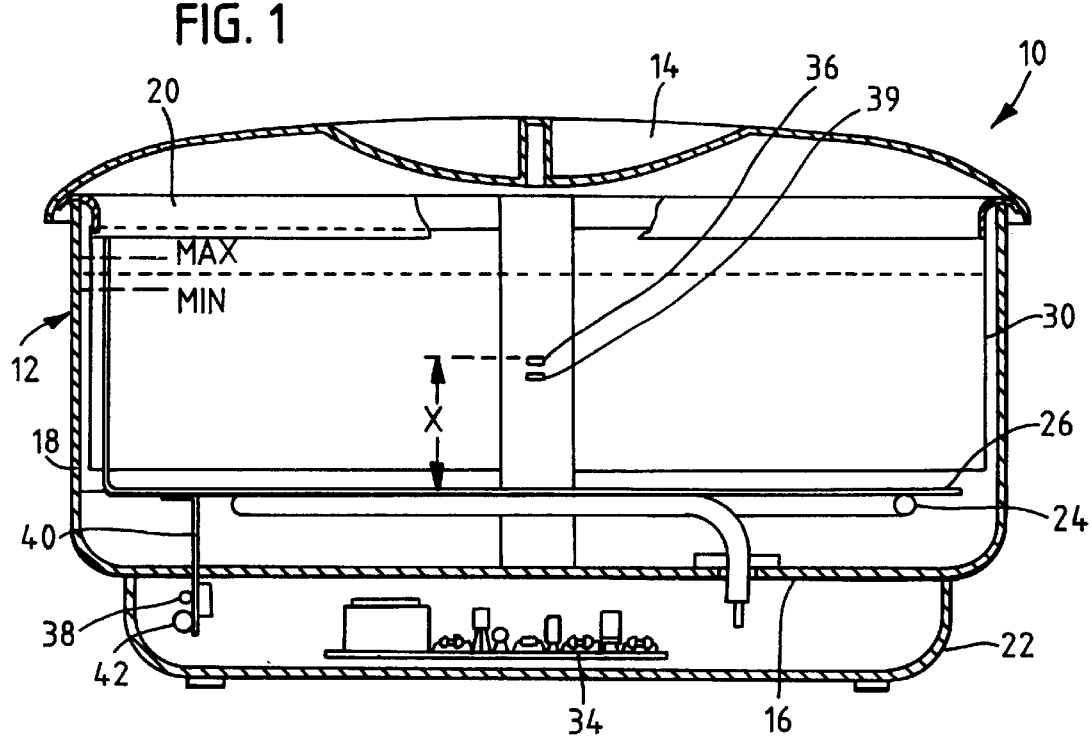
FIG. 1 is a side elevation view, in cross-section, of heat treatment apparatus in accordance with the teachings of the present invention.
Figure 4A:
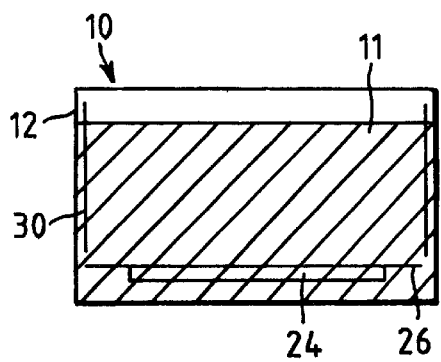
FIGS. 4A–4C are schematic illustrations showing progressive stages of a wax melting operation.

Referring initially to FIG. 1, a heat treatment apparatus in accordance with the teachings of the present invention is generally referred to with reference numeral 10. The apparatus 10 includes a housing 12, preferably formed of a plastic material, and a removable lid 14. A mass 11 of meltable heat treatment medium, such as paraffin wax, is disposed inside the housing 12 (FIG. 4A). The paraffin wax is normally in a solid state at room temperature, and therefore the apparatus 10 must heat the wax into a melted state. When the wax is melted, a user may submerge his or her hands, feet, elbows, or other body part in the wax. While the body part is placed in the bath, it is soothed, healed, or otherwise provided therapy.

In greater detail, the housing 12 includes a flat base 16 and a side wall 18 extending upwardly therefrom. A rounded rim 20 is attached to a top edge of the side wall 18 and is sized to seat the lid 14. A bottom enclosure 22 is attached to the base 16 for housing controls and other temperature sensitive components as described in greater detail below.

Figure 2:
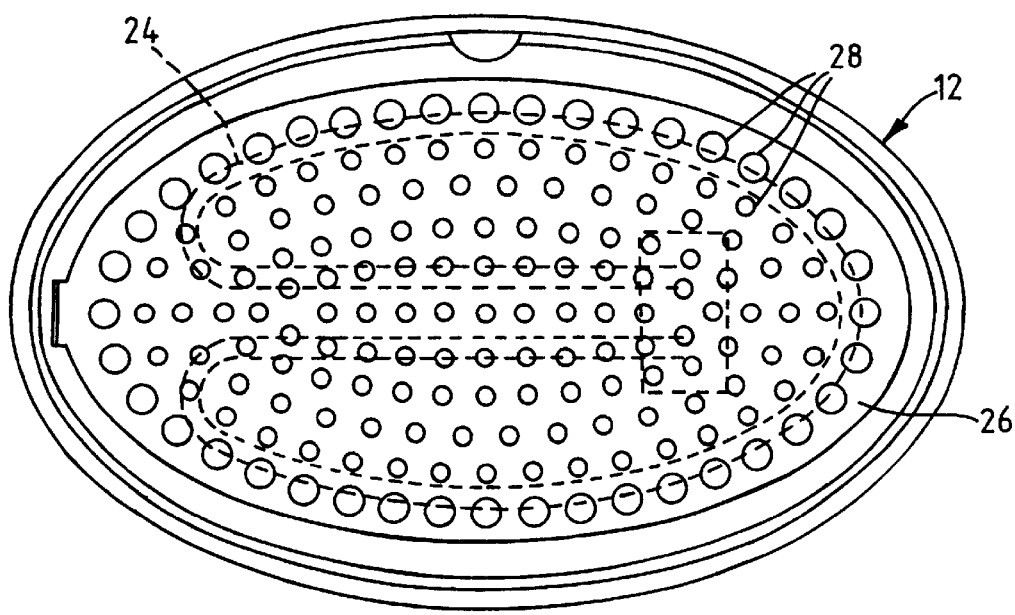
FIG. 2 is a top view of the heat treatment apparatus of FIG. 1 with the lid removed.

A heating element 24 is provided near the base 16 for melting paraffin wax deposited inside the housing 12. According to the illustrated embodiment, the heating element 24 is a tube heater. The heating element 24 is preferably operable at fast heat and keep warm settings, the benefits of which will be described in greater detail below. For example, the tube heater may be operable to generate approximately 550–600 watts at the fast heat setting, and approximately 300–500 watts at the keep warm setting. To help disperse heat from the heating element, a heat conducting plate 26 is positioned directly above the heating element 24. As is best shown in FIG. 2, the heat conducting plate 26 preferably includes a plurality of apertures 28 formed therethrough to allow paraffin wax to come into direct contact with the heating element 24. A heat conducting sleeve 30 is preferably provided inside the housing 12 near the side wall 18 for accelerating melting of an outer edge of the paraffin wax. In the illustrated embodiment, the heat conducting sleeve 30 is attached to a bottom edge of the rim 20. The heat conducting plate 26 and heat conducting sleeve 30 are preferably formed of a material having high thermal conductivity, such as aluminum.

Figure 3:
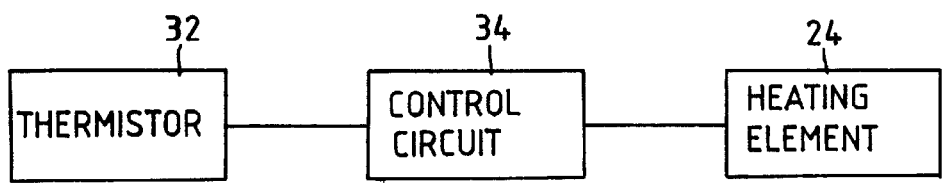
FIG. 3 is a schematic block diagram illustrating a temperature lube incorporated into the heat treatment apparatus.

Controls are provided for maintaining a desired temperature inside the housing 12. As shown schematically in FIG. 3, the controls generally comprise a thermistor 32 positioned inside the housing 12 and connected to a control circuit 34. The control circuit 34, in turn, is connected to the heating element 24. As is generally known in the art, the control circuit 34 operates the heating element 24 according to feedback provided by the thermistor 32.

The controls may include more than one thermistor for providing additional heat control features. As illustrated in FIG. 1, a fast heat thermistor 36 is located a distance "X", such as 4 centimeters, above the heat conducting plate 26 for measuring the temperature of the paraffin wax. The fast heat thermistor 36 is set at a shut-off temperature, such as 61° C. A keep warm thermistor 38 is attached to a bracket 40 connected to the heat conducting plate 26 for measuring the temperature of the heat conducting plate 26. The keep warn thermistor 38 preferably has low and high temperature limits, such as 55° C. and 57° C., respectively, to maintain the wax within a desired temperature range. Both of the thermistors 36, 38 are connected to the control circuit 34. A thermofuse 42 is also provided for controlling the amount of power supplied to the heating element 24 by cutting off power if the control circuit 34 malfunctions and overheating of the paraffin wax is detected. A safe temperature thermistor 39 may also be provided for indicating when the melted wax is at a safe usable temperature. The safe temperature thermistor 39 is set at a safe temperature limit, such as 61° C. Feedback from the safe temperature thermistor 39 is provided to the control circuit 34 which, in turn, is preferably connected to an indicating light (not shown), so that the indicating light is illuminated when the wax temperature is below the safe temperature limit.

Figure 4B:
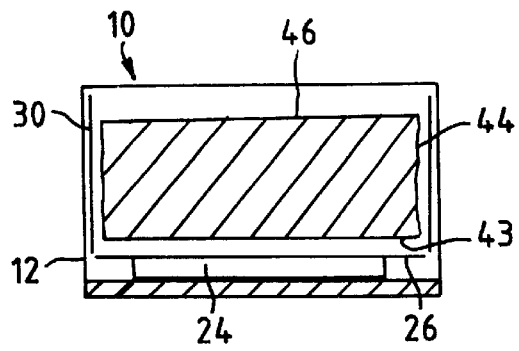

The heat treatment apparatus 10 may be operated in start-up and normal modes. During start-up mode, the apparatus 10 is operated to quickly melt the mass 11 of solid paraffin wax inside the housing 12 and to place the melted wax at a useable temperature. Before turning the apparatus 10 on, the housing 12 is filled with the mass 11 of solid paraffin wax (FIG. 4A). When the apparatus 10 is first turned on, the heating element 24 is preferably operated at the fast heat setting. As noted above, the heating element 24 is in direct contact with the paraffin wax so that the surrounding solid wax is rapidly melted. In addition, the heat conducting plate 26 distributes heat across a bottom surface 43 of the mass 11 of solid wax (FIG. 4B). The heat conducting sleeve 30 also disperses heat to melt an outer edge 44 of the solid wax mass 11. When the melted wax, having a temperature above the shut-off temperature, reaches the fast heat thermistor 36, the control circuit 34 shuts the heating element 24 off.

Figure 4C:
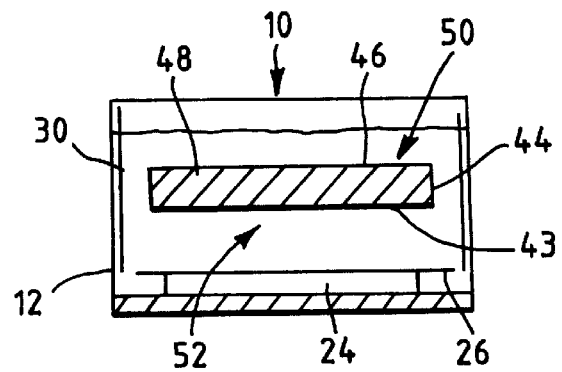

The clearance created by the sleeve 30 allows wax melted from the bottom surface 43 of the solid wax mass 11 to flow over and cover a top surface 46 of the mass 11. At this stage, a core 48 of solid wax is "sandwiched" between an upper layer of liquid wax 50 and a lower layer of liquid wax 52, as is best shown in FIG. 4C. Because the heating element 24 is off, only latent heat in the upper and lower layers 50, 52 of liquid wax is used to melt the remaining core 48 of solid wax. If the layers of liquid wax have insufficient heat to melt the remaining core 48, the keep warm thermistor 38 may be used to restart the heating element 24 until all the wax is melted. Typically, however, the upper and lower layers 50, 52 of liquid wax should have sufficient heat to melt the entire core 48 of solid wax.

When the solid wax core is sandwiched by the upper and lower layers 50, 52 of liquid wax, the temperature of the melted wax should be approximately 75° to 80° C. This temperature, while useful for rapidly melting the wax, is too high for therapeutic use and will burn the user. Because only the latent heat of the liquid wax layers is used to melt the remaining solid core 48, the temperature of the melted wax will rapidly drop as the core is melted. Eventually, the temperature of the wax will drop below the safe temperature limit, and the safe temperature thermistor 39 may be used to trigger the indicating light. At this temperature, the wax is safe for use.

After a sufficient quantity of the wax mass 11 is melted and a safe temperature is reached, the apparatus 10 will operate in the normal mode. In this mode, the heating element 24 is controlled using feedback from the keep warm thermistor 38 to maintain the melted wax bath within a desired temperature range, typically 55–57° C. During use, the temperature of the wax will drop while the heating element 24 is off until the low temperature limit is reached, at which time the keep warm thermistor 38 will trigger the control circuit 34 to operate the heating element 24. Once the high temperature limit is reached, the keep warm thermistor 38 triggers the control circuit 34 to shut off the heating element 24.

The heat treatment apparatus 10 preferably includes an insulating layer 54 positioned between the heating element 24 and bottom enclosure 22 for protecting the enclosure 22, and components disposed therein, from excessive heat. In the preferred embodiment, the insulating layer 54 is a bottom layer of solid wax deposited on the housing base 16 (FIGS. 4B and 4C). The bottom layer of solid wax is formed due to the fact that heat generated by the heating element 24 is generally directed upwardly. As a result, paraffin wax located below the heating element 24 will typically remain in a solid state and will not melt. This layer will absorb excess heat from the liquid wax, if present, thereby protecting the enclosure 22 from overheating. In addition, when the apparatus 10 is shut off, the heat absorption characteristics of the bottom layer will aid in dissipating a latent heat in the melted wax, thereby quickly lowering the temperature of the wax during cool-down.

From the foregoing, it will be appreciated that the heat treatment apparatus more quickly melts a solid mass of paraffin wax by creating upper and lower layers of melted wax which sandwich a remaining core of solid wax. Latent heat is then used to melt the remaining solid core and simultaneously lower the temperature of the melted wax to a usable level.

While the present invention has been described with reference to specific examples, which are intended to be illustrative only and not to be limiting of the invention, it will be apparent to those of ordinary skill in the art that changes, additions, and/or deletions may be made to the disclosed embodiments without departing from the spirit and scope of the invention.

What is claimed is:

1. A method of melting a mass of solid wax in a bath, the bath comprising a housing with a base and a sidewall, and a heating element disposed inside the housing near the base, the method comprising:

melting a bottom surface of the solid wax mass into a bottom layer of melted wax using the heating element;

shutting off the heating element once the bottom layer of melted wax reaches a desired volume;

transferring a portion of the bottom layer of melted wax to a top surface of the solid wax mass to create a top layer of melted wax, a remaining core of solid wax mass being disposed between the top and bottom layers of melted wax; and melting the remaining core of solid wax mass using latent heat in the top and bottom layers of melted wax, thereby to create a volume of melted wax at a usable temperature.

2. The method of claim 1, in which the bath further comprises a heat conducting plate located above the heating element to help melt the bottom surface of the solid wax max.

3. The method of claim 2, in which the heat conducting plate comprises a plurality of apertures.

4. The method of claim 1, in which the bath further comprises a sleeve disposed inside the housing adjacent the sidewall to help transfer the portion of the bottom layer of melted wax to the top surface of the solid wax max.

5. The method of claim 1, in which the volume of melted wax has a usable high temperature limit, wherein the heating element is operated at a temperature above the usable high temperature limit as the bottom surface is melted, and wherein a temperature of the top and bottom layers of the melted wax decreases below the usable high temperature limit as the remaining core of solid wax mass is melted using the latent heat.

6. The method of claim 5, in which a temperature sensor is located a known distance above the heating element, and in which the heating element is shut off when the bottom layer of melted wax reaches the temperature sensor.

7. Apparatus for melting a solid mass of wax comprising:

a housing having a base and a sidewall;

a heating element disposed inside the housing and positioned near the base for generating heat;

a heat conducting plate positioned above the heating element for conducting the heat from the heating element to melt a bottom surface of the solid mass of wax;

a heat conducting sleeve positioned inside the housing near the sidewall, and a control circuit for automatically controlling a temperature of the heating element.

8. The apparatus of claim 7, in which the heating element is operable at a fast heat setting and a keep warm setting.

9. The apparatus of claim 8, in which the heating element generates approximately 550–600 watts at the fast heat setting, and approximately 300–500 watts at the keep warm setting.

10. Apparatus for melting a solid mass of wax comprising:

a housing having a base and a sidewall;

a heating element disposed inside the housing and positioned near the base for generating heat;

a heat conducting plate positioned above the heating element for conducting the heat from the heating element to melt a bottom surface of the solid mass of wax, in which a plurality of orifices are formed in the heat conducting plate to place the heating element in contact with the wax; and a control circuit for automatically controlling a temperature of the heating element.

11. The apparatus of claim 10, in which an insulating layer of solid wax material forms below the heating element.

12. The apparatus of claim 11, further comprising an enclosure for the control circuit attached to the base of the housing, wherein the insulating layer of solid wax protects the enclosure from excessive heat.

13. Apparatus for melting a solid mass of wax comprising:

a housing having a base and a sidewall;

a heating element disposed inside the housing and positioned near the base for generating heat;

a heat conducting plate positioned above the heating element for conducting the heat from the heating element to melt a bottom surface of the solid mass of wax, in which a plurality of orifices are formed in the heat conducting plate to place the heating element in contact with the wax;

an enclosure attached to the housing base;

a control circuit for automatically controlling a temperature of the heating element disposed inside the enclosure; and an insulating layer positioned between the heating element and the enclosure for protecting the enclosure from excessive heat.

14. The apparatus of claim 13, in which the insulating layer comprises a layer of solid wax deposited on the housing base.

15. The apparatus of claim 13, in which the heating element is operable at a fast heat setting and a keep warm setting.

16. The apparatus of claim 15, in which the heating element generates approximately 550–600 watts at the fast heat setting, and approximately 300–500 watts at the keep warm setting.

17. Apparatus for melting a solid mass of wax comprising:

a housing having a base and a sidewall;

a heating element disposed inside the housing and positioned near the base for generating heat;

a heat conducting plate positioned above the heating element for conducting the heat from the heating element to melt a bottom surface of the solid mass of wax;

a heat conducting sleeve positioned inside the housing near the sidewall;

an enclosure attached to the housing base;

a control circuit for automatically controlling a temperature of the heating element disposed inside the enclosure; and an insulating layer positioned between the heating element and the enclosure for protecting the enclosure from excessive heat.

* * * * *